United States Patent
Ruben et al.

(10) Patent No.: US 10,464,836 B2
(45) Date of Patent: Nov. 5, 2019

(54) HERMETIC CONDUCTIVE FEEDTHROUGHS FOR A SEMICONDUCTOR WAFER

(71) Applicant: MEDTRONIC, INC., Minneapolis, MN (US)

(72) Inventors: David A. Ruben, Mesa, AZ (US); Michael S. Sandlin, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 992 days.

(21) Appl. No.: 14/050,415

(22) Filed: Oct. 10, 2013

(65) Prior Publication Data

US 2015/0101841 A1    Apr. 16, 2015

(51) Int. Cl.
```
C03B 23/20    (2006.01)
H05K 5/00     (2006.01)
A61N 1/375    (2006.01)
H01L 23/057   (2006.01)
H01L 23/10    (2006.01)
B81C 1/00     (2006.01)
```

(52) U.S. Cl.
CPC ............ C03B 23/20 (2013.01); A61N 1/3754 (2013.01); B81C 1/00301 (2013.01); H01L 23/057 (2013.01); H01L 23/10 (2013.01); H05K 5/0095 (2013.01); A61N 1/3756 (2013.01); B81B 2207/095 (2013.01); H01L 2924/0002 (2013.01)

(58) Field of Classification Search
CPC .... H05K 5/069; H05K 5/0095; H05K 5/0247; C03B 23/20

USPC ...................................................... 607/9, 36
See application file for complete search history.

(56) References Cited

U.S. PATENT DOCUMENTS

| | | |
|---|---|---|
| 3,624,460 A | 11/1971 | Correll |
| 4,587,144 A | 5/1986 | Kellerman et al. |
| 4,747,908 A | 5/1988 | Potter |
| 5,293,511 A * | 3/1994 | Poradish ............ G02B 26/0833 257/432 |
| 5,750,926 A * | 5/1998 | Schulman ............ A61N 1/3754 174/564 |
| 7,164,572 B1 | 5/2007 | Burdon |

(Continued)

FOREIGN PATENT DOCUMENTS

| | | |
|---|---|---|
| CN | 10124864 | 8/2008 |
| EP | 308557 A1 | 3/1989 |

(Continued)

OTHER PUBLICATIONS

(PCT/US2014/059886) PCT Notification of Transmittal of the International Search Report and the Written Opinion of the International Searching Authority.

*Primary Examiner* — Amanda K Hulbert
*Assistant Examiner* — Roland Dinga (57) ABSTRACT

A glass wafer has an internal surface and an opposing external surface separated by a wafer thickness. A hermetic, electrically conductive feedthrough extends through the wafer from the internal surface to the opposing external surface. The feedthrough includes a feedthrough member having an inner face exposed along the internal surface for electrically coupling to an electrical circuit. The feedthrough member extends from the inner face partially through the wafer thickness to an exteriorly-facing outer face hermetically embedded within the wafer.

30 Claims, 6 Drawing Sheets

(56) References Cited

U.S. PATENT DOCUMENTS

| | | |
|---|---|---|
| 7,725,177 B2 | 5/2010 | Iyer |
| 7,920,915 B2 * | 4/2011 | Mann ............... A61N 1/0551 |
| | | 607/2 |
| 8,195,308 B2 | 6/2012 | Frank |
| 8,288,654 B2 | 6/2012 | Taylor |
| 8,295,929 B2 | 10/2012 | Fang |
| 8,538,530 B1 | 9/2013 | Orinski |
| 8,796,109 B2 | 8/2014 | Ruben et al. |
| 9,120,287 B2 | 9/2015 | Ruben et al. |
| 9,171,721 B2 | 10/2015 | Danzl et al. |
| 2001/0039374 A1 | 11/2001 | Schulman |
| 2002/0072778 A1 * | 6/2002 | Guck .................. A61N 1/08 |
| | | 607/36 |
| 2003/0109903 A1 * | 6/2003 | Berrang ............ A61N 1/375 |
| | | 607/36 |
| 2003/0143775 A1 | 7/2003 | Brady |
| 2004/0126953 A1 | 7/2004 | Cheung |
| 2006/0108675 A1 | 5/2006 | Colgan et al. |
| 2006/0192272 A1 | 8/2006 | Receveur |
| 2007/0107524 A1 | 5/2007 | O'Brien et al. |
| 2010/0244218 A1 | 9/2010 | Chai et al. |
| 2011/0031698 A1 | 2/2011 | Tziviskos |
| 2011/0091687 A1 | 4/2011 | Haque |
| 2011/0139484 A1 | 6/2011 | Koester et al. |
| 2011/0270099 A1 | 11/2011 | Ruben |
| 2012/0101540 A1 | 4/2012 | O'Brien |
| 2012/0197155 A1 | 8/2012 | Mattes |
| 2013/0100595 A1 | 4/2013 | Koester et al. |
| 2013/0118680 A1 | 5/2013 | Liu |

FOREIGN PATENT DOCUMENTS

| | | |
|---|---|---|
| WO | WO 97/06853 | 2/1997 |
| WO | WO 2012/015756 A2 | 2/2012 |

* cited by examiner

HERMETIC CONDUCTIVE FEEDTHROUGHS FOR A SEMICONDUCTOR WAFER

TECHNICAL FIELD

The disclosure relates to devices having hermetic, electrical feedthroughs in glass wafers.

BACKGROUND

Electrical feedthroughs provide an electrically conductive path extending from the interior of a sealed enclosure or housing to a point outside the enclosure. The conductive path through the feedthrough includes a conductor pin, wire or other conductive member or material, which is electrically insulated from the container if the container is formed from a conductive material. For example, a conductive feedthrough in an implantable medical device (IMD) provides an electrically conductive path from a connection point to electronic circuitry contained within the IMD enclosure or housing to a point outside the enclosure. The feedthrough member is sealed to the enclosure to prevent the ingress of blood or other body fluids which could damage IMD internal circuitry and cause device malfunction or failure. The junction between the enclosure and the conductive member of the feedthrough can be vulnerable to leakage into the IMD enclosure when it is implanted and exposed to body fluids.

An ongoing design goal of IMDs is overall size reduction to promote patient comfort and facilitate less invasive or minimally invasive implantation procedures. As the size is reduced, selection of feedthrough components becomes limited due to small size requirements, and manufacturability of hermetic feedthroughs becomes more challenging. Other devices, such as micro-electro mechanical systems (MEMS) devices, sensors or other miniaturized devices that operate in fluid conditions may require hermetic electrical feedthroughs. Accordingly, a need remains for an improved hermetic feedthrough and associated method of manufacturing.

SUMMARY

In general, the disclosure is directed towards a hermetic feedthrough in a glass wafer. A glass wafer having a first surface and an opposing second surface separated from the first surface by a wafer thickness includes a feedthrough member having a first face and a second face, the first face exposed along the first surface. The feedthrough member extends partially through the wafer thickness such that the second face is embedded within the glass wafer. An electrically conductive trace is at least partially embedded in the wafer extending away from the second face and electrically coupling the second face to an electrical connection point located along the second opposing surface.

In one embodiment, a device enclosure includes a recessed package defining a cavity for retaining an electrical circuit. A glass lid having an internal surface facing the cavity and an opposing external surface facing away from the cavity is sealed to the recessed package to enclose the electrical circuit. An electrically conductive feedthrough extends through the glass lid. The feedthrough includes a feedthrough member having an exteriorly-facing outer face embedded in the glass lid and an inner face. The inner face is electrically coupled to the electrical circuit. The feedthrough member extends from the inner face partially through the lid thickness to the outer face that is embedded within the lid. An electrically conductive trace is at least partially embedded in the lid and extends away from the outer face. The trace electrically couples the exteriorly-facing outer face to an electrical connection point located along the lid external surface.

In another example, a device, which may be an IMD or other device operating in a fluid environment, includes an electrical circuit and a hermetic enclosure having a package and a glass lid sealed to the package enclosing the electrical circuit. The enclosure includes a feedthrough in the glass lid. The feedthrough includes a feedthrough member having an exteriorly-facing outer face and an inner face. The inner face is electrically coupled to the electrical circuit. The feedthrough member extends from the inner face partially through the lid thickness to the outer face that is embedded within the lid. An electrically conductive trace is at least partially embedded in the lid and extends away from the outer face. The trace electrically couples the exteriorly-facing outer face to an electrical connection point located along the lid external surface.

A method of manufacturing a hermetic feedthrough in a glass wafer includes depositing an electrically conductive trace along an exteriorly-facing outer face of a feedthrough member extending through a base layer of the glass wafer and embedding the outer face of the feedthrough member and at least a portion of the electrically conductive trace within the glass wafer. The glass wafer may be a lid or other portion of a device enclosure.

These and other examples are disclosed in the following description. The details of one or more aspects of the disclosure are set forth in the accompanying drawings and the description below. Other features, objects, and advantages will be apparent from the description and drawings, and from the claims.

DETAILED DESCRIPTION

Figure 1:
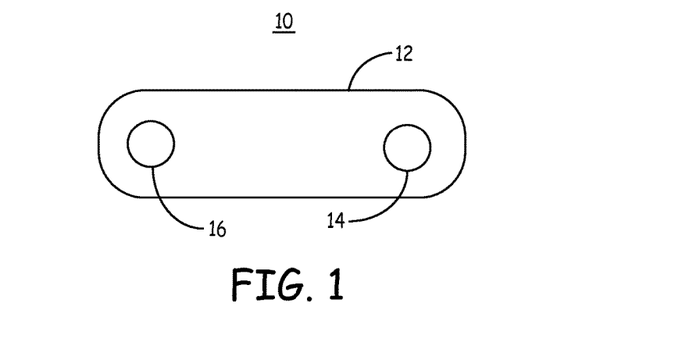
FIG. 1 is a conceptual diagram of an example IMD.

FIG. 1 is a conceptual diagram of an example device 10 that a feedthrough in a glass wafer may be implemented. In the example shown the device 10 is an IMD but could any of numerous types of devices that require a hermetic feedthrough. IMD 10 is shown embodied as a monitoring device having a pair of electrodes 14 and 16 located along an IMD enclosure 12. IMD enclosure 12 encloses electronic circuitry inside IMD 10 and protects the IMD circuitry from body fluids.

In some embodiments, enclosure 12 is manufactured using glass wafer technology. Enclosure 12, when formed of glass, or glass portions in combination with portions formed of other materials, is a sealable housing forming a hermetic barrier against body fluid ingress that could damage electronics packaged within enclosure 12. Electrical feedthroughs provide electrical connection of electrodes 14 and 16 across the hermetic barrier, provided by enclosure 12, to internal circuitry when electrodes 14 and 16 are positioned along the exterior surface of enclosure 12. Enclosure 12 may be formed of a silicate glass, e.g. borosilicate or aluminosilicate, fused silica, sapphire or other glass material. In some embodiments, enclosure 12 may include an outer coating over any portion of enclosure 12 to provide desired surface characteristics or features of IMD 10. In some embodiments, a portion of enclosure 12, such as an enclosure lid, is a glass wafer including one or more hermetic feedthroughs, and the other portions, for example a base and sidewalls, are formed of metal or a semiconductor.

IMD 10 may be embodied as an implantable cardiac monitor wherein electrodes 14 and 16 are used to sense biopotential signals, e.g. ECG signals. In alternative applications, electrodes 14 and 16 may be used for sensing any biopotential signal of interest, which may be, for example, an EGM, EEG, EMG, or a nerve signal, from any implanted location. IMD 10 may additionally or alternatively be configured to use electrodes 14 and 16 for measuring impedance across electrodes 14 and 16 when implanted in a patient's body.

Electrodes 14 and 16 may be formed of a biocompatible conductive material, e.g. titanium, platinum, iridium, or other metals or alloys thereof and may include other materials and/or coatings such as titanium nitride, platinum black or carbon black to improve conductivity or obtain other desired electrical and/or surface properties. The configuration illustrated in FIG. 1 is just one example electrode configuration. In other instances, sensing electrodes 14 and 16 may be located at other positions along IMD enclosure 12 than the positions shown in FIG. 1. Furthermore, electrodes 14 and 16 may be carried by a medical electrical lead extending from enclosure 12 and coupled to IMD internal circuitry via electrical feedthroughs.

A portion of enclosure 12 may function as an electrode and be insulated from any other electrodes positioned along enclosure 12. Although illustrated and described as being a cardiac monitor, IMD 10 may be any of a number of other implantable devices, including implantable hemodynamic monitors, blood chemistry monitors, pressure monitors, nerve monitors, muscle monitors, brain monitors, or the like. In any of these cases, IMD 10 may include other sensors besides or in addition to electrodes 14 and 16 to monitor desired physiological signals. In some embodiments, IMD 10 may be configured to deliver a therapy. For example, IMD 10 may be configured to deliver an electrical stimulation therapy via electrodes 14 and 16.

Moreover, a hermetic feedthrough as disclosed herein is not limited to implementation in an IMD. Numerous other devices, including MEMS devices, sensors, or other miniaturized devices for use in a fluid environment, which may be within the body of a living subject or other environments, may require a hermetic feedthrough and as such may implement a feedthrough as described herein.

Figure 2:
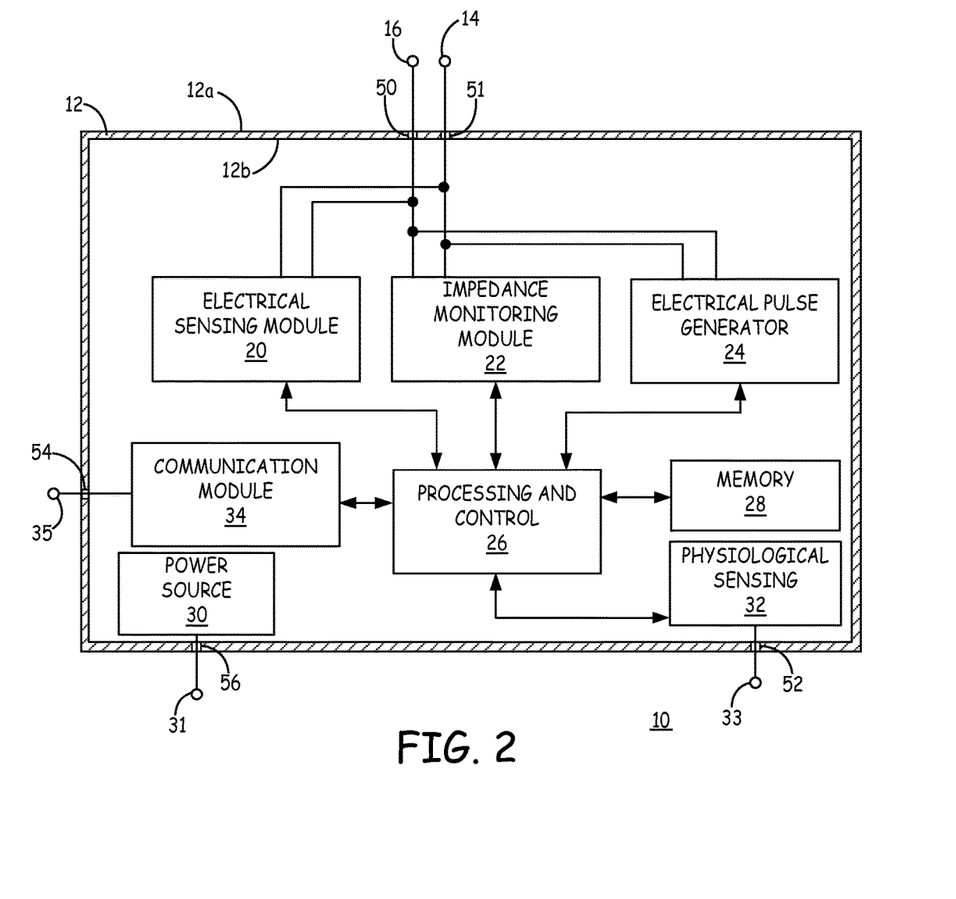
FIG. 2 is a functional block diagram of the IMD shown in FIG. 1.

FIG. 2 is a functional block diagram of IMD 10 shown in FIG. 1. In various embodiments, IMD 10 may include an electrical sensing module 20, an impedance monitoring module 22, and a pulse generator 24. Each of modules 20 and 22 may be coupled to electrodes 14 and 16 for sensing electrophysiological signals and/or monitoring impedance across electrodes 14 and 16. Pulse generator 24, if present, may be coupled to electrodes 14 and 16 for delivering electrical stimulation pulses to a patient, e.g. for delivering cardiac pacing, nerve stimulation, deep brain stimulation, or other neurostimulation.

In some embodiments, electrodes 14 and 16 are coupled to the various components within IMD 10 as required at appropriate times using switching circuitry controlled by processing and control module 26. In other examples, IMD 10 may include dedicated sensing electrodes coupled to sensing module 20 and impedance monitoring module 22 and dedicated therapy delivery electrodes coupled to pulse generator 24. More than one electrode pair may be provided for sensing additional signals and/or providing dedicated sensing and therapy delivery electrodes. Feedthroughs 50 and 51, shown schematically, provide electrically conductive pathways from each of electrodes 14 and 16 located exteriorly to enclosure 12, e.g. along the outer surface 12a of enclosure 12, to a component of electrical circuitry contained within enclosure 12, e.g. electrical sensing module, impedance monitoring module 22, and/or pulse generator 24.

In various examples, IMD 10 may include or be coupled to one or more physiological sensor(s) 33 for sensing signals other than biopotential or impedance signals. For example, sensor 33 may be a pressure sensor, acoustical sensor, optical sensor, temperature sensor, or other mechanical, optical, or chemical sensor that resides externally to enclosure 12. Sensor 33 is coupled to a physiological sensing module 32 residing internally to enclosure 12. A feedthrough 52 provides an electrically conductive pathway for electrically coupling sensor 33 to sensing module 32.

IMD 10 is shown to include a communication module 34 coupled to an antenna 35 for wireless data reception and/or transmission. In some examples, antenna 35 extends from communication module 34 located within IMD enclosure 12 to a point external to enclosure 12 to receive and/or transmit signals. A feedthrough 54 provides an electrically conductive pathway from a distal end of antenna 35 to communication module 34. Communication module 34 may be configured to transmit and receive communication signals via inductive coupling, electromagnetic coupling, tissue conductance, Near Field Communication (NFC), Radio Frequency Identification (RFID), BLUETOOTH®, WiFi, or other proprietary or non-proprietary wireless telemetry communication schemes.

A power source 30 provides power to IMD circuitry as needed. Power source 30 may include one or more energy storage devices, such as one or more rechargeable or non-rechargeable batteries. In one example, power source 30 is an inductively-coupled, rechargeable power source or inductively-coupled power transfer device. In such instances, power source 30 contained within enclosure 12 may be electrically coupled to an external antenna 31 for receiving an inductively-coupled power signal. A feedthrough 56 provides an electrically conductive pathway from antenna 31, which has a distal end exterior to enclosure 12, to the power source 30.

IMD 10 includes a processing and control module 26 and associated memory 28 to control IMD functions including processing signals received from electrodes 14 and 16 and other sensors 33 and controlling pulse generator 24 and communication module 34.

The various electrodes 14, 16, sensors 33 and antennae 31 and 35 illustrate the types of electrical components that may reside exteriorly to IMD enclosure 12 and require electrical connection to electrical circuitry contained within enclosure 12. In order to maintain the integrity of the internal circuitry, enclosure 12 is a hermetically sealed housing. As such, each of the feedthroughs 50, 51, 52, 54 and 56 provide a hermetically sealed, electrically conductive pathway through the wall of enclosure 12. Any of the feedthroughs 50, 51, 52, 54 and 56 may include a capacitive filter to provide filtering of external electromagnetic interference or other electrical noise that may contaminate electrical signals conducted to internal IMD circuitry via the respective feedthrough. A capacitor may be included in the integrated circuitry within enclosure 12 or along an inner surface 12b of enclosure 12.

The schematic diagram of IMD 10 shown in FIG. 1 is merely one example of an IMD that includes an electrical circuit or component within enclosure 12 (represented by functional blocks in FIG. 2) that is electrically coupled to at least one electrical component exterior to enclosure 12. Many other types or configurations of IMDs exist which may utilize a hermetic feedthrough as disclosed herein. IMD 10 may be a MEMS device, a sensor, a monitor for that receives and processes and/or stores signals, a therapy delivery device, or any combination thereof. Other examples of IMDs that could be configured to include a hermetic feedthrough as disclosed herein are generally described in U.S. Publication No. 2006/0192272 (Receveur), U.S. Publication No. 2012/0197155 (Mattes) and U.S. 2012/0101540 (O'Brien), all of which are incorporated herein by reference in their entirety.

Feedthroughs 50, 51, 52, 54 and 56 are shown extending through different sides of enclosure 12, for example a top side, a bottom side and a lateral side, in FIG. 2 for the sake of convenience. It is contemplated, however, that the various feedthroughs extending through a wall of enclosure 12 may alternatively be located along a single common side, such as a lid of the enclosure 12. Generally, feedthroughs extending through a glass portion of an IMD enclosure as disclosed herein may be located anywhere along the enclosure that is convenient for electrical connection to the internal device circuitry, convenient for electrical connection to an external component, such as an antenna, electrode or other sensor or other conductive element and/or simplifies manufacturing methods.

Figure 3:
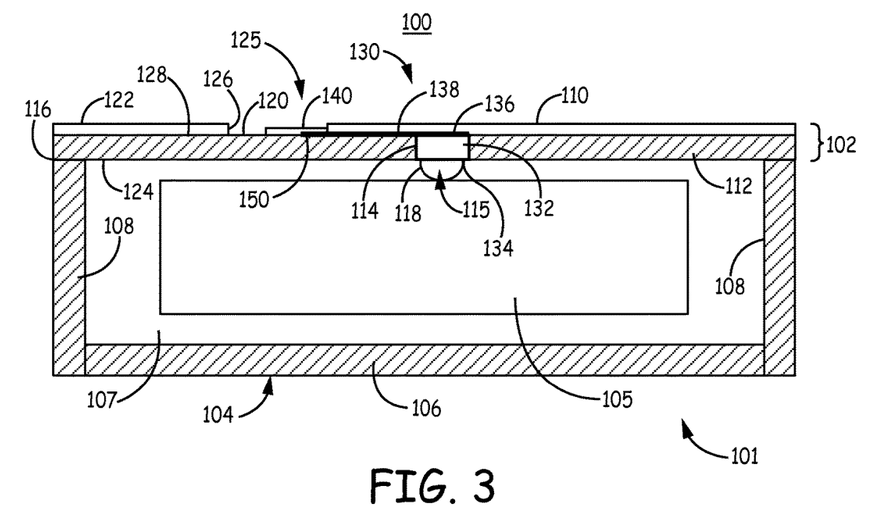
FIG. 3 is a schematic diagram of an IMD having a glass enclosure and an electrical feedthrough according to one embodiment.

FIG. 3 is a schematic diagram of a sectional view of an IMD 100 having a glass enclosure 101 and electrical feedthrough 130 according to one embodiment. Glass enclosure 101 includes a lid 102 and a recessed package 104 formed from glass wafers. Recessed package 104 has a bottom side 106 with a lateral sidewall 108 extending upward from and circumscribing bottom side 106 to define an interior cavity 107. Recessed package 104 may be formed from a glass wafer by etching, sand-blasting, machining or otherwise removing material from the wafer to form cavity 107 in some examples.

Recessed package 104 may be a single component or a multi-part component that is bonded or fused together. For example, sidewall 108 may be bonded or fused to bottom side 106 in a manufacturing assembly step. IMD circuitry 105 is located within cavity 107. Recessed package 104 and lid 102 are hermetically sealed at junction 116 between lateral side wall 108 and lid 102, e.g. by fusion bonding of the glass material or other methods. If package 104 is formed of another material such as a metal, the junction 116 may be sealed using soldering, brazing or other bonding methods.

Glass lid 102 is a multi-layer lid including at least a base layer 112 having an inner surface 124 facing interior cavity 107 of recessed package 104 and a top layer 110 having an external top surface 122 facing away from cavity 107. Base layer 112 and top layer 110 are hermetically sealed, e.g. by fusion bonding, along interface 128 to form a combined overall thickness of lid 102 that separates external top surface 122 from opposing inner surface 124.

Feedthrough 130 extends through lid 102. Base layer 112 includes a via 115 defined by interior sidewalls 114 extending from the inner surface 124 of base layer 112 to base layer top surface 120, at interface 128 between base layer 112 and top layer 110. In the example shown, sidewalls 114 are vertical sidewalls, extending approximately perpendicular to inner surface 124 and top surface 120. In other embodiments, sidewalls 114 may be angled and extend non-perpendicularly to inner surface 124. A feedthrough member 132 extends through via 115. Feedthrough member 132 is a conductive pin, wire or other conductive material filling, or at least partially filling, via 115 and bonded to the interior sidewalls 114 of base layer 112. Feedthrough member 132 may be any conductive metal or metal alloy, such as titanium, tungsten, niobium, copper, nickel, gold, platinum, iridium and solders such as PbSn or AuSn.

Feedthrough member 132 is formed of a conductive material that may have a thermal expansion coefficient that substantially matches the thermal expansion coefficient of base layer 112. Feedthrough member 132 may be deposited in via 115 as a solid component that is bonded to interior sidewalls 114, metallized or electroplated within via 115, or otherwise deposited to fill or partially fill via 115. In one example, feedthrough member 132 may be a tungsten or titanium member assembled in an appliance. A glass material, e.g. commercially available BOROFLOAT® or B270 Superwite® or other generic glasses as listed herein without limitation, may be heated and flowed around the feedthrough member 132 to simultaneously form via 115 and bond feedthrough member 132 to via sidewalls 114.

Feedthrough member 132 has an inner face 134, facing interiorly toward cavity 107, which is electrically coupled to electronic circuitry 105 via a conductive path 118. Conductive path 118 may be solder bump or connector pad that becomes aligned with a connection point on circuitry 105 when circuitry 105 is assembled within enclosure 101. The glass material of enclosure 101 may be selected to have a thermal coefficient of expansion that approximately matches the thermal coefficient of expansion of a silicon integrated circuit or other component of circuitry 105 to allow precise alignment between conductive path 118 and a respective connection point on circuitry 105. Matching thermal expansion coefficients between enclosure 101 and circuitry 105 enables reliable flip-chip connections to be made between circuitry 105 and feedthrough member 132 and protects stress-sensitive components, such as Hall-effect sensors or other sensors that may be included in circuitry 105.

In past practice, a feedthrough member typically extends entirely through an enclosure wall so that one end or face is exposed along an inner surface of the enclosure for electrical connection thereto and the other opposing end or face is exposed along an external surface of the enclosure for electrical connection thereto. In this way, the feedthrough may be a single continuous path from the inner surface to the outer surface of the enclosure. A bond between the sides of feedthrough member and the surrounding enclosure material (along the via sidewall) may be exposed to temperature cycling or other thermal changes. Thermal changes may compromise the bond between the two different materials and thus compromise the hermeticity of the enclosure when the feedthrough member is exposed to an external fluid environment.

In feedthrough 130, the exterior-facing outer face 136 of feedthrough member 132 is embedded in lid 102, between top layer 110 and base layer 112. An electrically conductive trace 138 extends from the feedthrough member outer face 136 to an open cavity 125 defined by interior sidewalls 126 of top layer 110. Open cavity 125 is open to the exterior of enclosure 101 and open to the top surface 120 of base layer 112, thereby exposing a portion of trace 138.

Trace 138 may be a thin film or layer of any electrically conductive material. In an IMD, trace 138 may be a biocompatible, biostable conductor such as titanium, niobium, tantalum, platinum or alloys thereof. In some embodiments, trace 138 may extend within a groove formed along top layer 110 and/or base layer 112 at interface 128 to maintain a level surface for bonding between top layer 110 and base layer 112.

Trace 138 is exposed in cavity 125 to provide an electrical connection point 150 for electrically coupling an external electrically conductive member 140 to feedthrough member 132. Electrically conductive member 140 may be a coupling member or contact pad to which an electrode or other sensor, antenna, or other external component is directly or indirectly electrically coupled. In some embodiments, an electrode or other external component may be mechanically coupled to top layer 110 within cavity 125 or along external top surface 122.

In various embodiments, conductive member 140 may wholly fill all of cavity 125 such that an electrode, sensor or other electrical component can be coupled to member 140 and extend along or away from external top surface 122 and enclosure 101. In other embodiments, conductive member 140 may fill a portion of cavity 125 and an electrode, sensor or other electrical component may fill the remainder of cavity 125 to extend flush with top surface 122 or protrude from top surface 122. In some embodiments, conductive member 140 is an electrode that fills cavity 125 and is directly coupled to trace 138 at connection point 150 without a separate coupling member. The cavity 125 provides a recess for retaining an electrode that is flush with or below top surface 122. By positioning an electrode or other sensor flush with or below top surface 122, the sensor is protected from tools or other handling or delivery objects during manufacturing and implantation procedures.

By embedding outer face 136 of feedthrough member 132 within lid 102, the bond between feedthrough member 132 and sidewalls 114 of via 115 is not directly exposed to body fluids or other external environment. Outer face 136 of feedthrough member 132 and at least a portion of trace 138 are embedded within lid 102 between top layer 110 and base layer 112 when layers 110 and 112 are fusion bonded along interface 128. By hermetically sealing outer face 136 and at least a portion of trace 138 within lid 102, the bond between sidewall 114 and feedthrough member 132 is protected from exposure to body fluids and the ingress of body fluids into enclosure cavity 107 along a path through feedthrough 130 is highly unlikely.

In the example shown, the feedthrough 130 does not include a ferrule. The feedthrough member 132 is bonded directly to the interior sidewall 114 of enclosure lid base layer 112. In other examples, a ferrule or other intermediate layer or coating may be used between feedthrough member 132 and interior sidewall 114 to enhance sealing between feedthrough member 132 and sidewall 114.

In the illustrative embodiments described herein, a hermetic feedthrough is shown extending through a lid of an IMD enclosure. It is contemplated that the IMD enclosure may have one or more feedthroughs extending through the lid 102 and/or a wall of the recessed package 104 of the enclosure. Furthermore, it is contemplated that lid 102 may be recessed along inner surface 124 such that lid 102 also forms a portion of the interior cavity 107. For example, recessed package 104 and lid 102 may be symmetrical.

Figure 4:
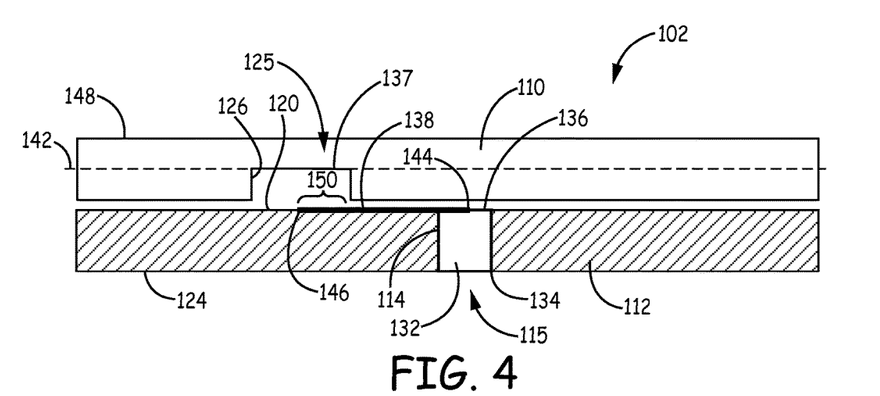
FIG. 4 is a schematic diagram depicting one method of manufacturing the IMD enclosure shown in FIG. 3.

FIG. 4 is a schematic diagram depicting one method for use in manufacturing enclosure 101 shown in FIG. 3. Lid 102 is assembled from a glass wafer top layer 110 and a glass wafer base layer 112. Base layer 112 includes a via 115 defined by an interior vertical sidewall 114 extending from lid inner surface 124 to a top, exterior-facing surface 120 of base layer 112. Feedthrough member 132 extends through via 115 from an inner face 134, which may be recessed from, flush with or protrude from inner surface 124, to an outer face 136 that is flush with top surface 120 of base layer 112. In various embodiments, solder bumps or other connection points may be provided along the inner face 134 of feedthrough member 132.

An electrically conductive trace 138 is deposited or printed along top surface 120 of base layer 112 in direct electrical contact with outer face 136 of feedthrough member 132. Trace 138 extends from a first end 144 directly coupled to outer face 136 of feedthrough member 132 to a second end 146 terminating within cavity 125 defined by top layer 110. In various embodiments, trace 138 may extend entirely across a width or diameter of top face 136 or less than a full width or diameter of top face 136. Trace 138 may extend across a full width or diameter of cavity 125 or a portion thereof.

Top layer 110 is fusion bonded or otherwise sealed to base layer 112 along base layer top surface 120. The top face 136 of feedthrough member 132, trace first end 144 and a portion of the mid-section of trace 138 that extends between the first end 144 and second end 146 are embedded between the top layer 110 and base layer 112 upon bonding the two layers 110 and 112 together. The distal end 146 of trace 138 is exposed within cavity 125 to provide an external electrical connection point 150, along the exposed portion of trace 138, to facilitate electrical coupling to feedthrough member 132. The electrical connection point 150 is laterally spaced apart from feedthrough member 132 and separated from feedthrough member outer face 136 by a hermetic bond between layers 110 and 112.

Top layer 110 is ground or machined down to a desired thickness and to expose cavity 125. A portion of top layer 110 is removed down to at least the recessed lateral surface 137 of cavity 125, e.g. down to dashed line 142, to open cavity 125 to the external environment. In some embodiments, the entire top surface 148 of top layer 110 is removed down to dashed line 142 to expose cavity 125 and form an open cavity as shown in FIG. 3. In other embodiments, only a portion of top layer aligned with cavity 125 may be removed from top surface 148 to extend cavity 125 by forming an opening in top surface 148, e.g. by laser drilling, thereby exposing cavity 125. Electrically conductive member 140 (shown in FIG. 3) may then be deposited or assembled in cavity 125 through a top opening of cavity 125, e.g. by metallization of the exposed top surface 120 of base layer 112. In other embodiments, conductive member 140 could be assembled or deposited into cavity 125 of the top layer glass wafer prior to bonding top layer 110 to base layer 112 and before grinding top surface 148.

In another example, cavity 125 may extend entirely through top layer 110 and may be previously formed through a glass wafer by laser drilling, sand-blasting or other removal methods to form top layer 110 with open cavity 125 defined by interior sidewall 126 prior to bonding to base layer 112. In each of these examples, however, connection point 150 of trace 138 is ultimately exposed to the outer environment surrounding enclosure 101 while feedthrough member top face 136 is embedded within lid 102 without being directly exposed to the exterior environment and without having an external component coupled directly to the feedthrough member 132. An external component, such as an antenna, electrode or other sensor, is only indirectly coupled to feedthrough member 132 via trace 138. The connection point 150 to trace 138 is along the external top surface 122 of lid 102 and spaced apart laterally from the embedded outer face 136 of feedthrough member 132. Via 115 extends only partially through lid 102 such that via 115 is terminated below the lid external top surface 122.

Figure 5:
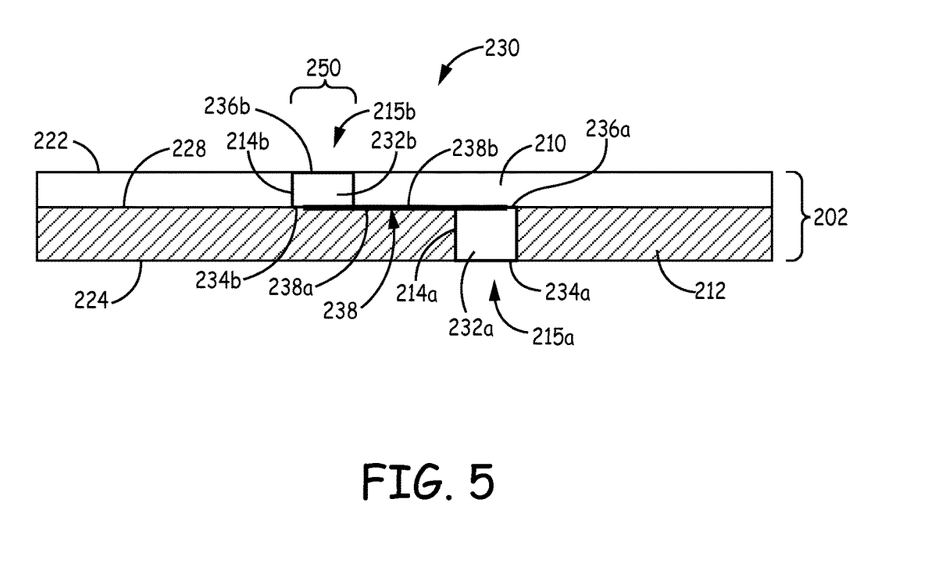
FIG. 5 is a schematic diagram of a glass lid of an IMD enclosure having a hermetic electrical feedthrough according to another embodiment.

FIG. 5 is a schematic diagram of a glass lid 202 of an IMD enclosure having a hermetic electrical feedthrough 230 according to another example. Glass lid 202 is formed from a glass wafer top layer 210 and a glass wafer base layer 212. Feedthrough 230 extends from an inner surface 224 of lid 202 to an external top surface 222. Feedthrough 230 includes a first feedthrough member 232a extending partially through lid 202 and a second feedthrough member 232b extending partially through lid 202 and laterally displaced from first feedthrough member 232a. First and second feedthrough members 232a and 232b are electrically coupled by a conductive trace 238a and 238b, collectively 238, embedded in lid 202, along interface 228 between top layer 210 and base layer 212.

First feedthrough member 232a extends between an exterior-facing, outer face 236a embedded within lid 202 and an interior-facing inner face 234a exposed along lid inner surface 224. Feedthrough member 232a is bonded to interior sidewall 214a defining via 215a. Via 215a extends from lid inner surface 224 only partially through lid 202, terminating beneath lid external surface 222, e.g. at interface 228 between base layer 212 and top layer 210.

Second feedthrough member 232b is laterally offset (spaced apart) from first feedthrough 232a. Second feedthrough member 232b has an interior-facing inner face 234b embedded within lid 202 and an exterior-facing outer face 236b exposed along lid external top surface 222. Outer face 236b of second feedthrough member 232b provides an electrical connection point 250 that is along the external top surface 222 of lid 202, opposite lid inner surface 224. When lid 202 is provided as part of an enclosure of an IMD, connection point 250 is a biostable, biocompatible surface. For example, feedthrough member 232b may be formed of titanium, tantalum, platinum, iridium or alloys thereof. In some embodiments, biocompatibility and biostability of connection point 250 may be improved by coating feedthrough member 232b, e.g. with carbon black, platinum black, platinum sputtering, titanium nitride or other coating.

Via 215b, defined by interior sidewall 214b, extends from lid external top surface 222 only partially through lid 202, terminating above lid inner surface 224, e.g. at interface 228 between base layer 212 and top layer 210. A central axis of via 215a and corresponding feedthrough member 232a is laterally offset from a central axis of via 215b and corresponding feedthrough 232b. Feedthrough members 232a and 232b are also vertically offset through lid 202 in that members 232a and 232b do not overlap each other in any horizontal plane extending through lid 202 parallel with inner surface 224 and external top surface 222.

Electrically conductive trace 238 is embedded within lid 202 along interface 228 and extends from embedded inner face 234b of feedthrough 232b to embedded outer face 236a of feedthrough 232a. Trace 238 may be deposited or printed along the top surface of base layer 212 and/or the bottom surface of top layer 210 such that when top layer 210 is] bonded to base layer 212, trace 238 is embedded within lid 202. In some embodiments, trace 238 may include two or more overlapping or partially overlapping traces 238a and 238b located along the top surface of base layer 212 and the bottom surface of top layer 210, respectively. Trace 238 may be a thin film to add negligible thickness along interface 228.

Figure 6:
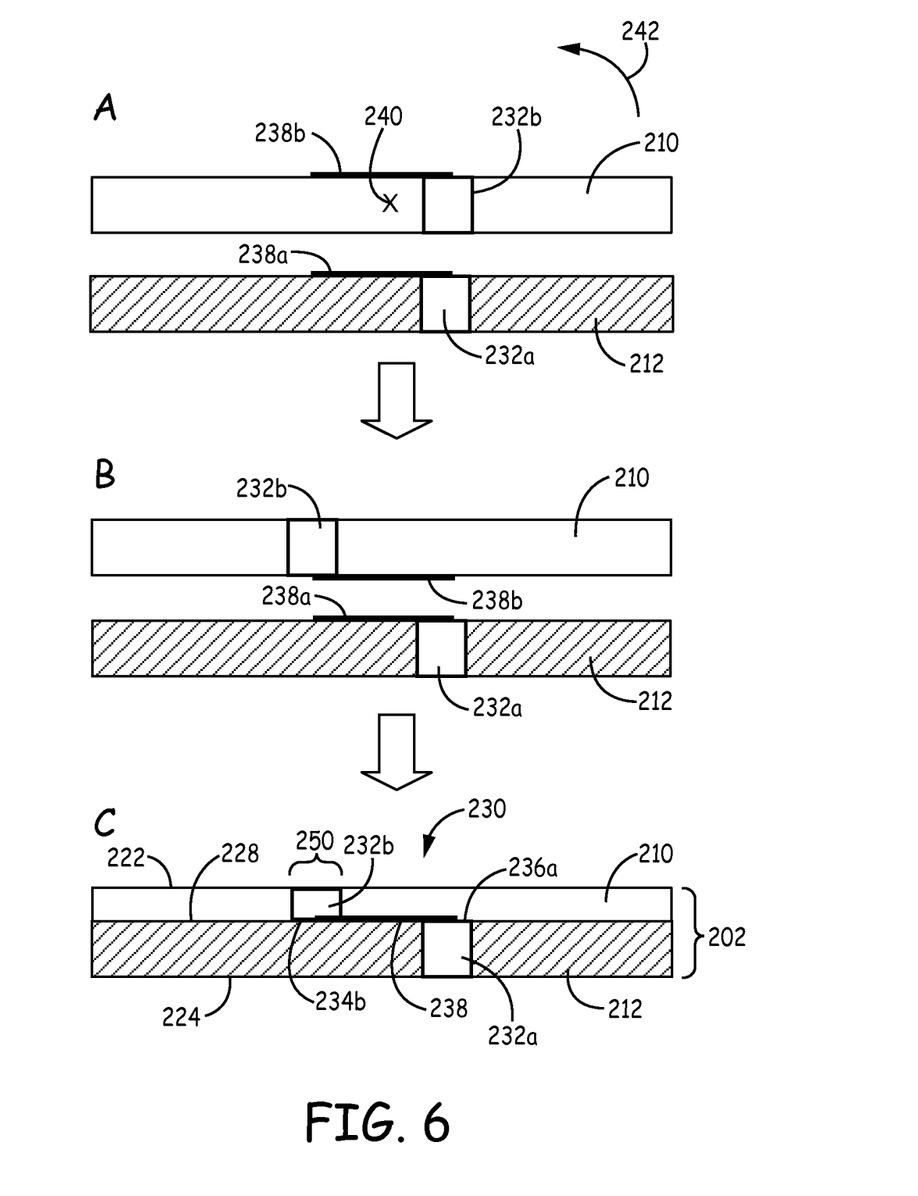
FIG. 6 is a schematic diagram of the lid shown in FIG. 5 during a manufacturing process.

FIG. 6 is a schematic diagram of lid 202 during a manufacturing process. Top layer 210 and bottom layer 212 may be formed from identical glass wafers having feedthrough members 232a and 232b extending completely through the respective wafers and traces 238a and 238b extending along one surface of each of the wafers, as shown in top panel A of FIG. 6. The wafer that becomes top layer 210 in lid 202 is flipped end-over-end by rotating the wafer in a direction indicated by arrow 242 on a z-axis, indicated by "x" 240, extending perpendicularly into the page.

The traces 238a and 238b are in overlapping, facing alignment as shown in panel B after flipping the top wafer in the manner described above. Feedthrough members 232a and 232b are no longer aligned with a common central axis. Feedthrough members 232a and 232b are laterally spaced apart from each other.

The top wafer that becomes top layer 210 and the bottom wafer that becomes base layer 212 are positioned against each other and fusion bonded or otherwise hermetically joined along interface 228 to form the bi-layer lid 202 shown in panel C. The bi-layer lid 202 has feedthrough 230 including two, laterally spaced apart feedthrough members 232a and 232b each having opposing outer and inner faces 236a and 234b, respectively, embedded within lid 202 along the hermetic interface 228. Traces 238a and 238b are aligned and overlap to form trace 238 that electrically couples feedthrough members 232a and 232b. Trace 238 is entirely embedded within hermetically fused interface 228 in this embodiment, but electrically couples feedthrough member 232a to an external connection point 250 by way of feedthrough member 232b.

A desired overall thickness of lid 202 may be achieved by grinding down the glass wafer that becomes top layer 210 to form lid external top surface 222. As shown in panel C, top layer 210 may have a final thickness that is less than the thickness of base layer 212.

The thickness of trace 238 is exaggerated in the drawings shown herein for the sake of clarity; it is recognized that trace 238 would be very thin such that it lies substantially flat along interface 228. For example trace 138 shown in FIG. 3 and trace 238 shown in FIG. 5 may be on the order of angstroms to microns thick while respective lids 102 and 202 may be approximately 3 millimeters or less in thickness. In some examples, lids 102 and 202 may be less than 1 millimeter in thickness, e.g. about 0.5 millimeters in thickness. The base layer 112 may be approximately 0.5 millimeters in thickness and the top layer 110 may be on the order of approximately 50 to 100 microns in thickness. In some examples given herein, the term "approximately" refers to a value within 10% of a stated value.

Figure 7:
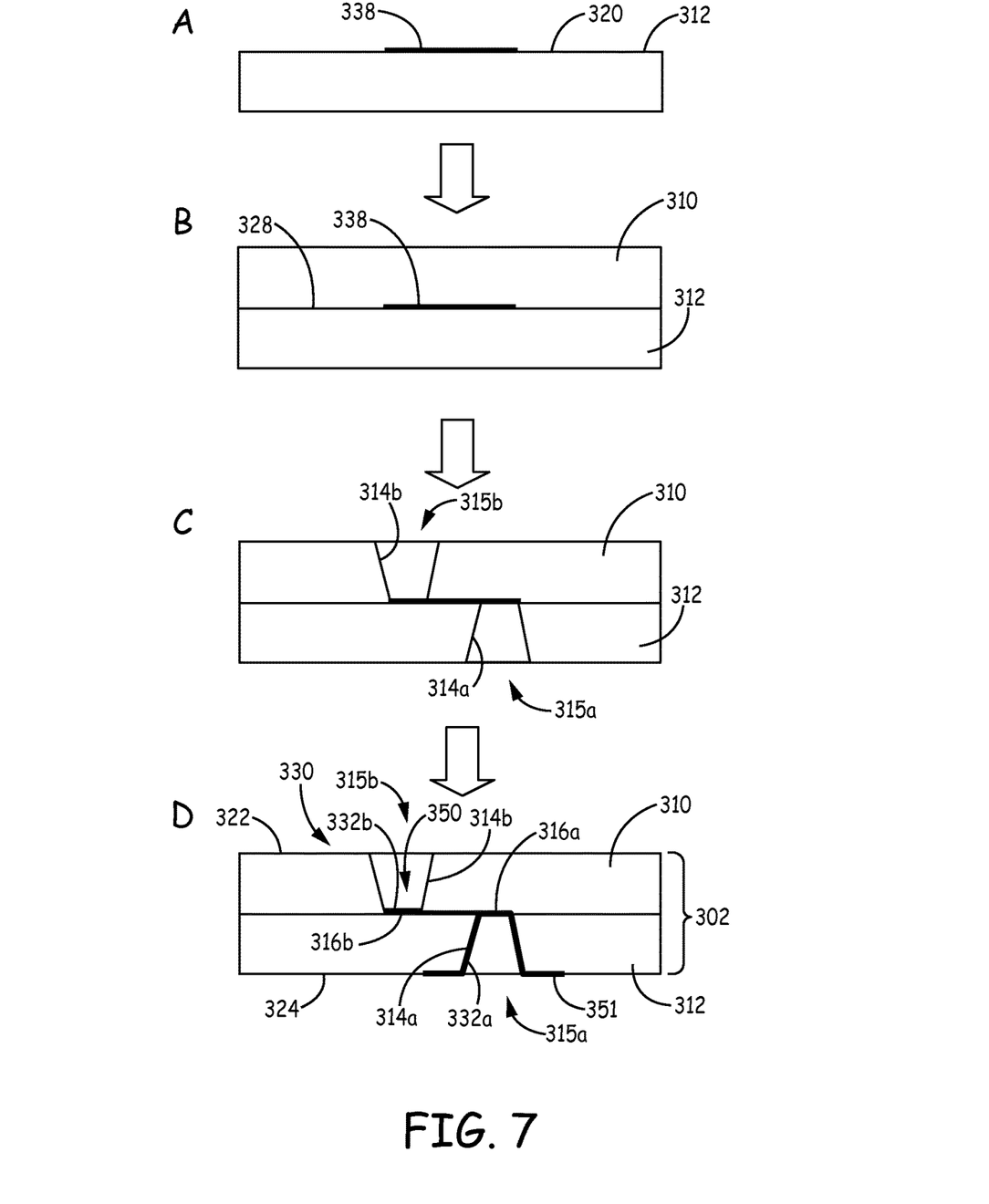
FIG. 7 is a schematic diagram of another example of a glass wafer having a hermetic feedthrough and a process of manufacture.

FIG. 7 is a schematic diagram of another example of a glass wafer having a hermetic feedthrough and an associated process of manufacture. An electrically conductive trace 338 is deposited on a top surface 320 of a glass wafer base layer 312 as shown in panel A. The trace 338 may be titanium, tungsten, tantalum, platinum, iridium, or other biocompatible, biostable metal or alloy thereof and may be printed, sputtered, metallized, electroplated or deposited using an evaporation process.

A wafer top layer 310 is bonded to the top surface 320 of base layer 312 (panel B) to hermetically seal top layer 310 to base layer 312, e.g. by fusion bonding. Trace 338 is embedded within the hermetic interface 328 formed between top layer 310 and base layer 312. In some embodiments a coating may be provided along the interface 328 to enhance bonding and/or planarize the top surface 320 after depositing trace 338 to improve the hermetic seal between top layer 310 and base layer 312. For example, in this and other embodiments disclosed herein, a coating of Silox or Teos (tetraethyl orthosilicate) or other binding sealant may be applied to top surface 320 of base layer 312 after positioning trace 338 along the top surface 320 using any of the methods listed above in preparation for bonding the two layers 310 and 312.

As shown in panel C, an inner via 315a and an outer via 315b are formed in the base layer 312 and top layer 310, respectively, by etching, laser drilling, or other removal method to form sidewalls 314a and 314b defining the vias 315a and 315b which both extend down to trace 338. Any non-conductive coating applied over trace 338 for planarization or other purposes may be etched away at least in a portion that will become exposed at the base 316b of via 315b. In other examples, vias 315a and 315b are formed through layers 312 and 310, respectively, prior to bonding the layers together.

Feedthrough members 332a and 332b are deposited in vias 315a and 315b, respectively (panel D) to form a glass wafer lid 302 having a hermetic feedthrough 330. Feedthrough members 332a and 332b may be formed by sputtering, electroplating, or other metallization techniques or combinations of techniques. In some embodiments, feedthrough members 332a and/or 332b may include a sputtered layer and a plated layer. Top surface 322 may be ground down to achieve a desired overall thickness of lid 302.

Sidewalls 314a and 314b are shown angled in this embodiment, which may facilitate metallization, sputtering or other processes used to deposit feedthrough members 332a and 332b in vias 315a and 315b. In various embodiments, a feedthrough member is deposited as a film or layer along at least the base of the via and may extend up the via sidewall. As an example, feedthrough member 332b is shown along base 316b of via 315b providing an external contact point 350 for electrical coupling to an embedded exteriorly-facing outer face of feedthrough member 332a. The feedthrough member 332a extends along via 315a along its base 316a, sidewall 314a and out of via 315a along inner surface 324 of base layer 312. The extent that feedthrough members 332a and 332b extend along via sidewalls 314a and 314b and inner surface 324 or external top surface 322 may vary between embodiments and may depend on what external electrical components are being coupled to feedthrough 330, their location relative to feedthrough 330, and methods used for coupling to an electrical circuit housed by an associated enclosure of which lid 302 is a portion. For example, portions of feedthrough member 332a that extend along inner surface 324 may provide electrical coupling points 351 for electrically coupling to an electrical circuit that will be enclosed in a hermetic enclosure.

When feedthrough members 332a and 332b extend along external top surface 322 or inner surface 324, non-conductive coatings may be applied over a portion of the feedthrough member to define a conductive electrode or contact pad area. For example, a coating of parylene, silicone, deposited glass or other non-conductive coating may be applied to define insulated and non-insulated portions of feedthrough member(s) 332a and/or 332b.

Figure 8:
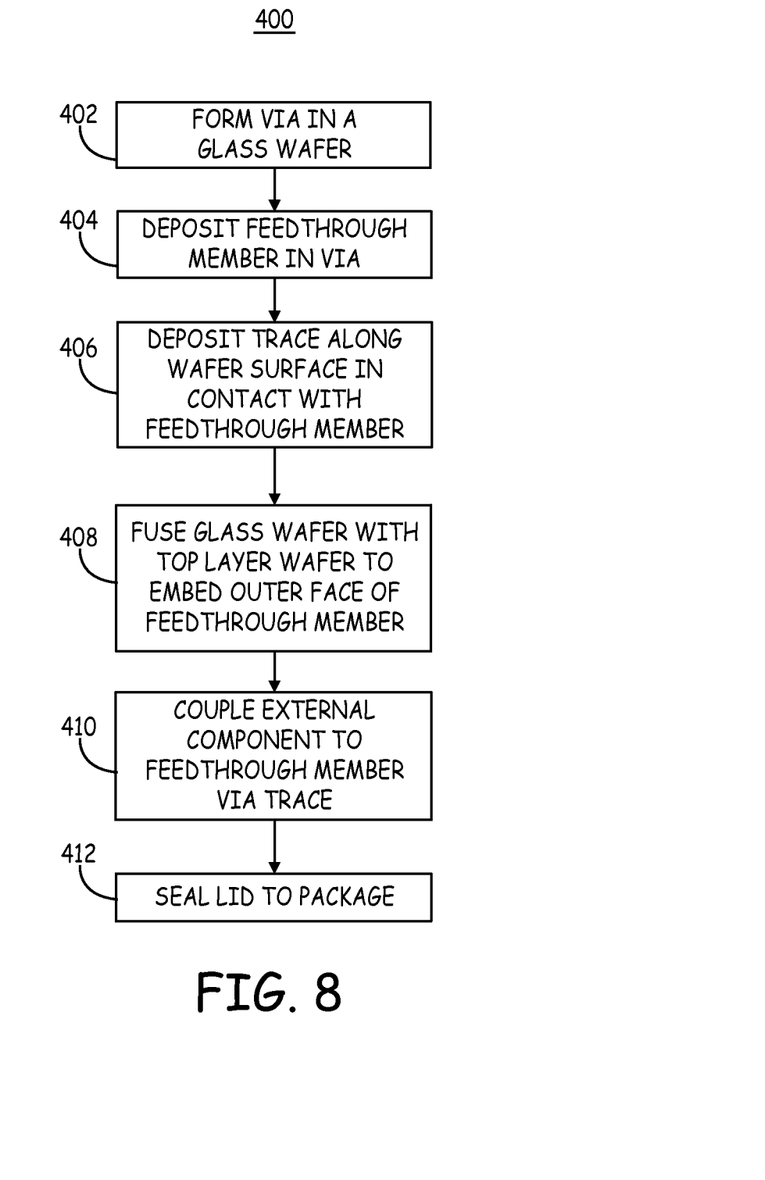
FIG. 8 is a flow chart of a method for manufacturing a glass lid of an IMD enclosure having a hermetic electrical feedthrough.

FIG. 8 is a flow chart 400 of a method for manufacturing an IMD enclosure having a hermetic electrical feedthrough according to one example. At block 402, a via is formed in a glass wafer that will become a base layer of a lid of the enclosure. A via hole in a glass wafer may be formed by laser drilling or sandblasting. The via is defined by an interior sidewall, which may be vertical or angled, formed in the glass wafer at a desired location. At block 404 a conductive feedthrough member is deposited in the via. For example, the feedthrough member may be any conductive metal such as titanium, tungsten, niobium, copper, nickel, gold, platinum, and solders such as PbSn or AuSn. The feedthrough member may be deposited in the via by electroplating, metallization, as a solid pre-formed member or other deposition methods. In some examples, via formation at block 402 and deposition of the feedthrough member at block 404 is achieved in a single step by positioning the feedthrough member, e.g. a titanium or tungsten pin, in an assembly and flowing the glass material of the glass wafer around the feedthrough member.

An electrically conductive trace is deposited along a top surface of the glass wafer at block 406, e.g. by printing, sputtering, evaporating, electroplating or other methods, so that the trace extends along an exposed outer face of the feedthrough member. At block 408, the glass wafer is bonded with a second glass wafer that becomes the top layer of the lid. The outer face of the feedthrough member in the base layer and at least a portion of the conductive trace deposited on the top surface of the base layer are embedded in the bonded interface between the two glass wafers. In some examples, as shown in FIG. 7, embedding a conductive trace in a layered glass wafer may be performed prior to forming a via and depositing a feedthrough member in the via. Accordingly, the particular order of the blocks shown in FIG. 8 are not intended to convey any limitations regarding a particular order of steps performed in a manufacturing process but merely indicate processes and aspects of steps that are included to arrive at a glass wafer having a hermetic feedthrough extending from an inner wafer surface to an opposing external top wafer surface and including an embedded feedthrough member face.

An external component is coupled to the embedded feedthrough member face via the trace at block 410. The external component, e.g. an electrode or other sensor, may be assembled onto an external connection point provided by the trace. In some embodiments, an external component may be a metallized contact pad or other component. In some examples, e.g. as shown in FIG. 4, a cavity is formed in the second glass wafer, e.g. by sand blasting, laser drilling or machining, that extends partially through the second glass layer. The cavity is aligned with a portion of the trace but is laterally offset from the embedded outer face of the first feedthrough member. Upon fusing or bonding the two glass wafers together, a portion of the trace is exposed within the cavity of the second wafer providing an external electrical connection point while the remainder of the trace is embedded within the hermetically bonded interface, extending laterally toward the embedded feedthrough outer face.

A top surface of the wafer may be ground down to create open access to the cavity and the connection point along the exposed portion of the trace. The exposed portion of the trace is an external connection point enabling electrical connection to the embedded face of the feedthrough member. The connection point is spaced apart laterally from the embedded exteriorly-facing outer face of the feedthrough member by the trace that extends laterally along the fused interface away from embedded feedthrough outer face. The feedthrough member extends only through the glass wafer forming the lid base layer, from the inner surface of the lid to a top surface of the base layer.

In another example, a second feedthrough member is deposited in a via formed in the second glass wafer that becomes the lid top layer to make electrical contact with the trace upon fusing the first base layer wafer to the second top layer wafer. The second feedthrough member may extend from a bottom surface of the top layer to the lid external top surface and is spaced apart laterally from the embedded outer face of the first feedthrough member. The exposed external face of the second feedthrough member is an external connection point for electrically coupling an external component, e.g. an electrode, contact pad, sensor or other electrically conductive member, to the embedded face of the first feedthrough member by an electrical path including the second feedthrough member and the trace. An interiorly-facing inner face of the second feedthrough member in the top glass wafer becomes embedded within the lid upon fusing the two glass wafers. The second glass wafer may be identical to the first glass wafer as shown in the example depicted in FIG. 6.

The top glass wafer may be ground down to a thickness that is less than the thickness of the bottom glass wafer to achieve a desired lid thickness. The second feedthrough member may be deposited in the cavity of the second glass wafer before or after grinding the top layer down to a desired thickness.

The lid is sealed to a recessed package at block 412. The package may be formed from the same glass material as the lid or another material, e.g. silicon, metal or other biocompatible material. For example, the lid and the package may both be cut from a silicate glass wafers, sapphire, or fused silica. In other examples, the package may include a semiconductor material or a metal. Appropriate sealing techniques are used at block 412 according to the material(s) of the package and lid. If both the package and the lid are glass, they may be fusion bonded. In some examples, a coating or interlayer may be applied at the interface between the lid and the recessed package to facilitate formation of a reliable hermetic seal.

A hermetic cavity is defined by the sealed glass lid and package for retaining and protecting an electrical circuit. The glass lid has an internal surface facing the cavity and an opposing external surface facing away from the cavity and separated from the internal surface by the lid thickness. Solder bumps or other connection pads may be applied at the bottom face of the lid base layer in contact with the feedthrough member to facilitate connection to an electrical circuit to be contained within the enclosure.

In some examples, the electrical circuit is assembled onto the internal lid surface prior to sealing the lid to the package. When the lid is positioned over the recessed package, the electrical circuit is positioned within the recessed package. In other examples, solder bumps or other electrical contacts make electrical connection to an electrical circuit already residing within the recessed package upon placing the lid on the package.

The external connection point of the lid enables an external electrical component to be electrically coupled to the internal electrical circuit. For example, an electrode or other sensor may be electrically coupled to the external connection point, before or after sealing the lid to the package, which becomes electrically coupled to the electrical circuit assembled onto the internal surface of the lid or when the lid is sealed in place onto the recessed package. The enclosure manufactured with a glass wafer lid having a hermetic feedthrough can be incorporated into a wafer fabrication processes, using wafer fab tools, processes and materials which can significantly improve IMD reliability and reduce manufacturing cost.

Thus, various embodiments of a glass wafer having a hermetic feedthrough have been described. However, one of ordinary skill in the art will appreciate that various modifications may be made to the described embodiments without departing from the scope of the claims. Such modifications may include altering the order of manufacturing steps performed or combinations of features an enclosure, glass wafer and/or feedthrough in different combinations than those shown and described herein. These and other examples are within the scope of the following claims.

The invention claimed is:

1. An enclosure, comprising:
    a glass lid having an internal surface facing an internal cavity of the enclosure and an opposing external surface facing away from the cavity and separated from the internal surface by a lid thickness, wherein the glass lid comprises:
        a glass wafer base layer defining the internal surface;
        a glass wafer top layer defining the external surface; and
        a hermetically sealed interface between the glass wafer base layer and the glass wafer top layer along the surface that is embedded within the lid, wherein the glass wafer base layer is fusion bonded to the glass wafer top layer; and
    an electrically conductive feedthrough extending through the glass lid, the feedthrough comprising:
        a first feedthrough member having an inner face electrically coupled to an electrical circuit, the first feedthrough member extending from the inner face partially through the lid thickness to an exteriorly-facing outer face embedded within the lid; and
        an electrically conductive trace at least partially embedded in the lid, extending away from the exteriorly-facing outer face along a surface embedded within the lid and electrically coupling the exteriorly-facing outer face to an electrical connection point located along the lid external surface.

2. The enclosure of claim 1, wherein the connection point is spaced apart laterally from the embedded exteriorly-facing outer face.

3. The enclosure of claim 1, wherein the feedthrough member extends from the internal surface to the interface.

4. The enclosure of claim 3, wherein the trace extends laterally along the interface.

5. The enclosure of claim 3, wherein the top layer comprises a second feedthrough member extending from the interface to the lid external surface, the second feedthrough member spaced apart laterally from the first feedthrough member,
    the trace embedded in the lid and extending from the exteriorly-facing outer face of the first feedthrough member to the second feedthrough member.

6. The enclosure of claim 5, wherein the second feedthrough member comprises an interiorly-facing inner face embedded within the lid.

7. The enclosure of claim 1, wherein the top layer comprises an interior sidewall extending from the lid external surface to a top surface of the base layer,
the connection point being along a portion of the trace exposed within the cavity.

8. The enclosure of claim 7, further comprising a sensor positioned in the cavity and electrically coupled to the trace.

9. The enclosure of claim 1, wherein the top layer has a first thickness and the base layer has a second thickness greater than the first thickness.

10. The enclosure of claim 1, further comprising a planarization coating extending along the surface that is embedded within the lid for planarizing the electrically conductive trace along the surface that is embedded within the lid.

11. An implantable medical device, comprising:
an electrical circuit; and
a hermetic enclosure defining a cavity for retaining the electrical circuit and comprising:
a glass lid having an internal surface facing the cavity and an opposing external surface facing away from the cavity and separated from the internal surface by a lid thickness, wherein the glass lid comprises:
a glass wafer base layer defining the internal surface;
a glass wafer top layer defining the external surface; and
a hermetically sealed interface between the glass wafer base layer and the glass wafer top layer along the surface that is embedded within the lid, wherein the glass wafer base layer is fusion bonded to the glass wafer top layer; and
an electrically conductive feedthrough extending through the glass lid, the feedthrough comprising:
a first feedthrough member having an inner face electrically coupled to the electrical circuit, the first feedthrough member extending from the inner face partially through the lid thickness and to an exteriorly-facing outer face embedded within the lid, and
an electrically conductive trace at least partially embedded in the lid, extending away from the exteriorly-facing outer face along a surface embedded within the lid and electrically coupling the exteriorly-facing outer face to an electrical connection point located along the lid external surface.

12. The device of claim 11, wherein the connection point is spaced apart laterally from the embedded exteriorly-facing outer face.

13. The device of claim 11, wherein the feedthrough member extends from the internal surface to the interface.

14. The device of claim 13, wherein the trace extends laterally along the interface.

15. The device of claim 13, wherein the top layer comprises a second feedthrough member extending from the interface to the lid external surface, the second feedthrough member spaced apart laterally from the first feedthrough member,
the trace embedded in the lid and extending from the exteriorly-facing outer face of the first feedthrough member to the second feedthrough member.

16. The device of claim 15, wherein the second feedthrough member comprises an interiorly-facing inner face embedded within the lid.

17. The device of claim 11, wherein the top layer comprises an interior sidewall defining a cavity extending from the lid external surface to a top surface of the base layer,
the connection point being along a portion of the trace exposed within the cavity.

18. The device of claim 17, further comprising a sensor positioned in the cavity and electrically coupled to the trace.

19. The device of claim 11, wherein the top layer has a first thickness and the base layer has a second thickness greater than the first thickness.

20. The device of claim 11, wherein the glass lid comprises at least one of a silicate glass, borosilicate, aluminosilicate, fused silica, and sapphire.

21. The device of claim 11, further comprising a planarization coating extending along the surface that is embedded within the lid for planarizing the electrically conductive trace along the surface that is embedded within the lid.

22. A glass wafer having a first surface and an opposing second surface separated from the first surface by a wafer thickness, the wafer comprising:
a first feedthrough member having a first face and a second face, the first face exposed along the first surface and extending partially through the wafer thickness and the second face embedded within the glass wafer;
an electrically conductive trace at least partially embedded in the wafer extending away from the second face along a surface embedded within the wafer and electrically coupling the second face to an electrical connection point located along the second opposing surface;
a glass wafer base layer defining the first surface;
a glass wafer top layer defining the second surface; and
a hermetically sealed interface between the glass wafer base layer and the glass wafer top layer along the surface that is embedded within the wafer, wherein the glass wafer base layer is fusion bonded to the glass wafer top layer.

23. The glass wafer of claim 22, wherein the connection point is spaced apart laterally from the embedded first face.

24. The glass wafer of claim 22, wherein the trace extends laterally along the interface.

25. The glass wafer of claim 22, wherein the top layer comprises an interior sidewall defining a cavity extending from the second surface to a top surface of the base layer,
the connection point being along a portion of the trace exposed within the cavity.

26. The glass wafer of claim 25, further comprising a sensor positioned in the cavity and electrically coupled to the trace.

27. The glass wafer of claim 22, wherein the top layer comprises a second feedthrough member extending from the interface to the second surface, the second feedthrough member spaced apart laterally from the first feedthrough member,
the trace embedded in the glass wafer and extending from the first face of the first feedthrough member to the second feedthrough member.

28. The glass wafer of claim 27, wherein the second feedthrough member comprises a face embedded within the glass wafer.

29. The glass wafer of claim 22, wherein the top layer has a first thickness and the base layer has a second thickness greater than the first thickness.

30. The glass wafer of claim 22, further comprising a planarization coating extending along the surface that is embedded within the wafer for planarizing the electrically conductive trace along the surface that is embedded within the wafer.

* * * * *